United States Patent
Hossainy et al.

(10) Patent No.: US 7,247,364 B2
(45) Date of Patent: *Jul. 24, 2007

(54) COATING FOR IMPLANTABLE MEDICAL DEVICES

(75) Inventors: Syed F. A. Hossainy, Fremont, CA (US); Yiwen Tang, San Jose, CA (US); Andrew C. Tung, Castro Valley, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/067,375

(22) Filed: Feb. 25, 2005

(65) Prior Publication Data

US 2005/0143808 A1    Jun. 30, 2005

Related U.S. Application Data

(62) Division of application No. 10/375,620, filed on Feb. 26, 2003, now Pat. No. 6,926,919.

(51) Int. Cl.
| | |
|---|---|
| B32B 7/02 | (2006.01) |
| A61L 27/00 | (2006.01) |
| A61L 27/26 | (2006.01) |
| A61L 27/52 | (2006.01) |
| A61L 27/54 | (2006.01) |

(52) U.S. Cl. .................. 428/212; 428/480; 428/34.1; 623/1.44; 623/1.46; 623/1.49; 623/11.11; 623/23.57; 623/23.58; 623/23.59

(58) Field of Classification Search ............. None
See application file for complete search history.

(56) References Cited

U.S. PATENT DOCUMENTS

| | | |
|---|---|---|
| 2,072,303 A | 3/1937 | Hermann et al. |
| 4,329,383 A | 5/1982 | Joh |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,941,870 A | 7/1990 | Okada et al. |
| 4,977,901 A | 12/1990 | Ofstead |
| 5,061,424 A | 10/1991 | Karimi et al. |
| 5,084,315 A | 1/1992 | Karimi et al. |
| 5,112,457 A | 5/1992 | Marchant |
| 5,165,919 A | 11/1992 | Sasaki et al. |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,480,436 A * | 1/1996 | Bakker et al. ................. 600/37 |
| 5,508,036 A * | 4/1996 | Bakker et al. ............... 424/424 |
| 5,569,463 A | 10/1996 | Helmus et al. |
| 5,578,073 A | 11/1996 | Haimovich et al. |
| 5,605,696 A | 2/1997 | Eury et al. |
| 5,609,629 A | 3/1997 | Fearnot et al. |
| 5,624,411 A | 4/1997 | Tuch |
| 5,628,730 A | 5/1997 | Shapland et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,679,400 A | 10/1997 | Tuch |
| 5,700,286 A | 12/1997 | Tartaglia et al. |
| 5,702,754 A | 12/1997 | Zhong |
| 5,716,981 A | 2/1998 | Hunter et al. |
| 5,735,897 A | 4/1998 | Buirge |
| 5,746,998 A | 5/1998 | Torchilin et al. |
| 5,776,184 A | 7/1998 | Tuch |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,851,508 A | 12/1998 | Greff et al. |
| 5,858,746 A | 1/1999 | Hubbell et al. |
| 5,865,814 A | 2/1999 | Tuch |
| 5,869,127 A | 2/1999 | Zhong |

(Continued)

FOREIGN PATENT DOCUMENTS

EP    0 301 856    2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Vivian Chen
(74) *Attorney, Agent, or Firm*—Squire, Sanders & Dempsey L.L.P.

(57) ABSTRACT

An implantable medical device, such as a stent, is disclosed having a coating. The coating includes a poly(butylene terephthalate-co-ethylene glycol)polymer. The coating can also include a drug.

14 Claims, No Drawings

U.S. PATENT DOCUMENTS

| | | |
|---|---|---|
| 5,871,437 A | 2/1999 | Alt |
| 5,873,904 A | 2/1999 | Ragheb et al. |
| 5,876,433 A | 3/1999 | Lunn |
| 5,877,224 A | 3/1999 | Brocchini et al. |
| 5,897,955 A | 4/1999 | Drumheller |
| 5,925,720 A | 7/1999 | Kataoka et al. |
| 5,955,509 A | 9/1999 | Webber et al. |
| 5,957,879 A | 9/1999 | Roberts et al. |
| 5,971,954 A | 10/1999 | Conway et al. |
| 5,980,928 A | 11/1999 | Terry |
| 5,980,948 A * | 11/1999 | Goedemoed et al. ........ 424/489 |
| 5,980,972 A | 11/1999 | Ding |
| 5,997,517 A | 12/1999 | Whitbourne |
| 6,010,530 A | 1/2000 | Goicoechea |
| 6,015,541 A | 1/2000 | Greff et al. |
| 6,031,028 A | 2/2000 | Iino et al. |
| 6,033,582 A | 3/2000 | Lee et al. |
| 6,040,415 A | 3/2000 | Arimori et al. |
| 6,042,875 A | 3/2000 | Ding et al. |
| 6,051,576 A | 4/2000 | Ashton et al. |
| 6,051,648 A | 4/2000 | Rhee et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,153,252 A | 11/2000 | Hossainy et al. |
| 6,165,212 A | 12/2000 | Dereume et al. |
| 6,203,551 B1 | 3/2001 | Wu |
| 6,218,016 B1 | 4/2001 | Tedeschi et al. |
| 6,231,600 B1 | 5/2001 | Zhong |
| 6,240,616 B1 | 6/2001 | Yan |
| 6,245,753 B1 | 6/2001 | Byun et al. |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,346,110 B2 | 2/2002 | Wu |
| 6,358,556 B1 | 3/2002 | Ding et al. |
| 6,379,381 B1 | 4/2002 | Hossainy et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,494,862 B1 | 12/2002 | Ray et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,527,801 B1 | 3/2003 | Dutta |
| 6,527,863 B1 | 3/2003 | Pacetti et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 * | 9/2003 | Castro et al. ................ 118/669 |
| 6,620,194 B2 | 9/2003 | Ding et al. |
| 6,656,216 B1 * | 12/2003 | Hossainy et al. .......... 623/1.13 |
| 6,663,662 B2 * | 12/2003 | Pacetti et al. ............... 623/1.13 |
| 6,685,957 B1 * | 2/2004 | Bezemer et al. ............. 424/426 |
| 6,706,408 B2 | 3/2004 | Jelle |
| 6,896,965 B1 * | 5/2005 | Hossainy .................. 428/411.1 |
| 6,926,919 B1 * | 8/2005 | Hossainy et al. .......... 427/2.25 |
| 2001/0008965 A1 | 7/2001 | Kinn et al. |
| 2001/0018469 A1 | 8/2001 | Chen et al. |
| 2001/0037145 A1 | 11/2001 | Guruwaiya et al. |
| 2001/0051832 A1 * | 12/2001 | Bakker et al. ............ 623/23.58 |
| 2002/0077693 A1 | 6/2002 | Barclay et al. |
| 2002/0091433 A1 | 7/2002 | Ding et al. |
| 2002/0111693 A1 * | 8/2002 | Hesseling et al. ........ 623/23.48 |
| 2002/0128378 A1 * | 9/2002 | Bezemer et al. ............. 524/601 |
| 2002/0155212 A1 | 10/2002 | Hossainy |
| 2002/0161371 A1 * | 10/2002 | Bezemer et al. ............... 606/72 |
| 2003/0065377 A1 | 4/2003 | Davila et al. |
| 2003/0099712 A1 | 5/2003 | Jayaraman |
| 2005/0025799 A1 * | 2/2005 | Hossainy et al. ........... 424/423 |
| 2005/0106204 A1 * | 5/2005 | Hossainy et al. ........... 424/423 |
| 2005/0112170 A1 * | 5/2005 | Hossainy et al. ........... 424/423 |
| 2005/0137381 A1 * | 6/2005 | Pacetti ...................... 528/272 |
| 2005/0191332 A1 * | 9/2005 | Hossainy .................... 424/423 |
| 2005/0214339 A1 * | 9/2005 | Tang et al. ................. 424/423 |
| 2005/0223062 A1 * | 10/2005 | Hossainy et al. ............ 427/2.1 |
| 2005/0233062 A1 * | 10/2005 | Hossainy et al. ............ 427/2.1 |
| 2005/0237971 A1 * | 10/2005 | Skraparlis .................. 370/329 |
| 2005/0238686 A1 * | 10/2005 | Hossainy et al. ........... 424/423 |
| 2006/0078588 A1 * | 4/2006 | Hossainy .................... 424/423 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 068 872 A1 * | 1/2001 |
| EP | 1 273 314 | 1/2003 |
| JP | 2001-190687 | 7/2001 |
| WO | WO 91/12846 | 9/1991 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |

| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

COATING FOR IMPLANTABLE MEDICAL DEVICES

CROSS REFERENCE

This Application is a divisional of application Ser. No. 10/375,620, filed Feb. 26, 2003, U.S. Pat. No. 6,926,919.

BACKGROUND OF THE INVENTION

1. Field of the Invention

This invention is directed to coatings for drug delivery devices, such as drug delivery vascular stents. More particularly, the invention is directed to a poly(butylene terephthalate-co-ethylene glycol) coated device.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, the properties of stent coatings can be improved. For example, when the outermost layer of the coating comprises a blend of hydrophobic and hydrophilic polymers, the hydrophobic polymers tend to bloom to coating-air interface. Yet, in many applications it is highly desirable to have hydrophilic polymers evolve at the coating-air interface to provide the stent coating with better blood compatibility, biological activity and non-fouling properties. Accordingly, the present invention discloses such improved stent coatings and methods for fabricating thereof.

SUMMARY

In one embodiment of the invention an implantable medical device is disclosed comprising a coating—the coating includes a poly(butylene terephthalate-co-ethylene glycol) polymer. The implantable medical device can be a stent. In some embodiments, the ratio between the units derived from ethylene glycol and the units derived from butylene terephthalate is between about 0.67:1 and 9:1. In some embodiments, the coating includes therapeutic substance such as paclitaxel, docetaxel, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, and 40-O-tetrazole-rapamycin, and analogs thereof. In some embodiments, the ethylene glycol units constitute 40 to 90 molar % of the polymer.

In accordance with another embodiment an implantable medical device is provided comprising a coating, the coating including a first region comprising poly(butylene terephthalate-co-ethylene glycol)polymer and a second region comprising poly(butylene terephthalate-co-ethylene glycol) wherein the mole % of the ethylene glycol is higher in the second region than the first region. In some embodiments, the second region is over the first region. In some embodiments, the second region is the outermost layer of the coating. The first region can be the reservoir layer including a drug position beneath the second region.

DETAILED DESCRIPTION

A coating for an implantable medical device, such as a stent, according to one embodiment of the present invention, can include a drug-polymer layer (also referred to as "reservoir" or "reservoir layer") or alternatively a polymer free drug layer, an optional primer layer and an optional topcoat layer. The drug-polymer layer serves as a reservoir for the drug. The reservoir layer or the polymer free drug layer can be applied directly onto the stent surface. The optional topcoat layer, which can be essentially free from any drugs, serves as a rate limiting membrane which helps to control the rate of release of the drug. The optional primer layer can be applied on the stent surface to improve the adhesion of the drug-polymer layer or the polymer free drug layer to the stent.

The reservoir layer and the optional primer and topcoat layers of the coating can be formed on the stent by dissolving a polymer or a blend of polymers in a solvent, or a mixture of solvents, and applying the resulting polymer solution on the stent by spraying or immersing the stent in the solution. To incorporate a drug into the reservoir layer, the drug in a form of a solution can be combined with the polymer solution. Alternatively, to fabricate a polymer free drug layer, the drug can be dissolved in a suitable solvent or mixture of solvents, and the resulting drug solution can be applied on the stent by spraying or immersing the stent in the drug solution.

Instead of introducing the drug in a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art will select the suitable solvent to form the solvent phase of the suspension, as well as the quantity of the drug to be dispersed in the solvent phase. The suspension can be mixed with a polymer solution and the mixture can be applied on the stent as described above. Alternatively, the drug suspension can be applied on the stent without being mixed with the polymer solution.

The outermost layer of the stent coating can be either the topcoat layer or the reservoir layer (if the optional topcoat layer is not used). The outermost layer of the stent coating is comprised of a blend of polymers, the blend to include one or more hydrophilic polymers and one or more hydrophobic polymers. The mass ratio between the hydrophilic and hydrophobic polymers in the outermost layer of the coating can be typically between about 1:100 and 1:9.

Generally, hydrophobicity of a polymer can be gauged using the Hildebrand solubility parameter δ. The term "Hildebrand solubility parameter" refers to a parameter measuring the cohesion of a substance. The δ parameter is determined as follows:

$$\delta = (\Delta E/V)^{1/2}$$

where δ is the solubility parameter, $(cal/cm^3)^{1/2}$;
$\Delta E$ is the energy of vaporization, cal/mole; and
V is the molar volume, $cm^3$/mole.

Whichever polymer in the polymer blend has lower δ value compared to the δ value of the other polymer in the blend is designated as a hydrophobic polymer, and the polymer with higher δ value is designated as hydrophilic. If more than two polymers are used in the blend, then each can be ranked in order of its δ value. For the practice of the present invention, the value of δ of a particular polymer is inconsequential for classifying a polymer as hydrophobic or hydrophilic so long as the difference in the δ values of the two polymers is sufficient to allow the hydrophilic polymer to migrate or bloom to the surface as described below. In one exemplary embodiment, the δ value defining the boundary between the hydrophobic and hydrophilic components of the polymer blend can be about $11(cal/cm^3)^{1/2}$.

Poly(ethylene-co-vinyl alcohol) (EVAL) is one example of a typical polymer that can be utilized as a hydrophobic component of the polymer blend used to fabricate the reservoir layer or the topcoat layer. EVAL can be used to make the optional primer layer as well. EVAL is a product of hydrolysis of ethylene-vinyl acetate copolymers and has the general formula —[CH$_2$—CH$_2$]$_m$—[CH$_2$—CH(OH)]$_n$—. EVAL may also include a terpolymer having up to about 5 molar % of units derived from styrene, propylene and other suitable unsaturated monomers. A brand of copolymer of ethylene and vinyl alcohol distributed commercially under the trade name EVAL by Aldrich Chemical Co. of Milwaukee, Wis., can be used.

Other examples of hydrophobic polymers and hydrophilic that can be used include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly(vinylidene fluoride-co-hexafluoro propene), poly(vinyl pyrrolidone), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alpha-olefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of some solvents suitable for making the stent coatings include N,N-dimethylacetamide (DMAC), N,N-dimethylformamide (DMF), tetrahydrofurane (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., a 50:50 by mass mixture);

(2) water, i-propanol, and DMAC (e.g., a 10:3:87 by mass mixture);

(3) i-propanol and DMAC (e.g., 80:20, 50:50, or 20:80 by mass mixtures);

(4) acetone and cyclohexanone (e.g., 80:20, 50:50, or 20:80 by mass mixtures);

(5) acetone and xylene (e.g. a 50:50 by mass mixture);

(6) acetone, FLUX REMOVER AMS, and xylene (e.g., a 10:50:40 by mass mixture); and (7) 1,1,2-trichloroethane and chloroform (e.g., a 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

Following the formation of the outermost layer of the stent coating comprising a blend of hydrophobic and hydrophilic polymer(s), the surface of the coating can be treated to enrich the surface with hydrophilic polymer(s). In order to enrich the surface with hydrophilic polymer(s), various methods of treatment of the stent coating can be used. According to one method of the post-coating treatment, the coated stent can be exposed to the environment of a humidifying chamber. The length of such treatment can be between about 12 hours and 28 hours, for example, about 24 hours, at a temperature of between about 40° C. and about 80° C., more narrowly, between about 45° C. and about 60° C., for example, about 50° C. and relative humidity of between about 90% and about 100%. Any commercially available humidifying chamber can be used. As a result of the exposure of the stent to high humidity levels at elevated temperatures, water is expected to be deposited on the surface of the stent coating. Water will gradually extract the hydrophilic polymer to the coating surface leading to migration of the hydrophilic polymer and its blooming to the coating-air interface.

According to another method of the post-coating treatment, the coated stent can be physically placed on a film of a hydrogel, for example, a poly(vinyl alcohol) hydrogel, and gently rolled back and forth a number of times covering the entire circumference of the stent. For example, the coated stent can be rolled in the described fashion between 5 and 10 times, while a pressure of between about 1 atm and 3 atm is applied to the stent when it is being rolled. The physical contact between the film of the hydrogel and the stent coating can alter the coating-air interface, resulting in extraction of the hydrophilic polymer and its blooming to the coating-air interface.

According to yet another method of the post-coating treatment, the coated stent can be cooled at a temperature between about 4° C. and about −20° C. for a period of time between about 30 minutes and about 2 hours. Following the cooling process, the stent can be either exposed to ambient air for about 24 hours, or treated in the humidifying chamber as described above. This procedure is expected to lead to condensation of water on the surface of the coating, resulting in extraction of the hydrophilic polymer and its blooming to the coating-air interface.

Optionally, any combination of the three methods of the post-coating treatment described above can be used, if desired. As another option, following the post-coating treatment, the coated stent can be heated to a temperature which is about equal to the glass transition temperature ($T_g$) of the hydrophobic component of the coating.

In another embodiment, instead of a blend of a hydrophobic and hydrophilic polymer, an interpenetrating polymer network (IPN) can be used to make the outermost layer of the stent coating, the IPN includes at least one hydrophobic component and at least one hydrophilic component. For the purposes of the present invention, the definition of the IPN used by the International Union of Pure and Applied Chemistry (IUPAC) is adopted. The IUPAC describes the IPN as a polymer comprising two or more networks which are at least partially interlaced on a molecular scale, to form both chemical and physical bonds between the networks. The networks of an IPN cannot be separated unless chemical bonds are broken. In other words, an IPN structure represents two or more polymer networks that are partially chemically cross-linked and partially physically entangled. One example of an IPN that can be used is a surface hydrogel.

One example of a product that can be used for forming the IPN is a PEG-based unsaturated product, for example, pre-polymer of PEG-acrylate or PEG-methacrylate having a general formula $CH_2=CX-COO-[CH_2-CH_2-O]_n-H$, where X is hydrogen (acrylates) or methyl (methacrylates). The molecular weight of PEG-acrylate or methacrylate can be within a range of about 10,000 to 100,00 Daltons. PEG-acrylate or PEG-methacrylate prepolymer can be applied on the surface of the drug-polymer layer or topcoat layer and cured, for example, using a radical initiator which is activated by UV radiation (UV initiators), light (light initiators), or heat (thermal initiators). Examples of appropriate initiators include acetophenone, 2,2-dimethoxy-2-phenol-acetophenone (UV initiators), camproquinone, ethyl-4-N,N,-dimethyl aminobenzoate (light initiators), and benzoyl peroxide (thermal initiator). As a result of the curing process, PEG-acrylate or PEG-methacrylate will partially cross-link and partially physically entangle with the polymer of the underlying drug-polymer layer thus forming the outermost coat layer which includes an IPN. PEG-acrylate or PEG-methacrylate is intended to broadly include poly(ethylene glycol)-diacrylate (PEG-diacrylate) and poly(ethylene glycol)-dimethacrylate (PEG-dimethacrylate). PEG-acrylate or PEG-methacrylate and PEG-diacrylate or PEG-dimethacrylate can be optionally terminated, for example, with stearic acid, to form PEG-acrylate-stearate or PEG-methacrylate-stearate, respectively.

Examples of other products that can be used for forming the IPN include such unsaturated reactive products as N-vinylpyrrolidone, heparin and its derivatives, hyaluronic acid and its derivatives, some hydrogel-forming products such as poly(butyleneterephthalate-co-ethylene glycol) (PBT-PEG), and mixtures of any of these products with each other or with PEG-acrylate or PEG-methacrylate. A type of PBT-PEG polymers is also known under a trade name POLYACTIVE and is available from IsoTis Corp. of Holland.

After the IPN-based outermost coating has been formed, it can be subjected to a post-coating treatment to cause blooming or migration of the hydrophilic component of the IPN to the coating-air interface. For example, any method of the post-coating treatment described above, or any combination thereof, can be used.

One kind of an IPN is a hydrogel. If it is desirable to include a hydrogel in the outermost layer of the stent coating, PBT-PEG can be used as a hydrogel-forming product. PBT-PEG can be utilized for fabricating not only the outermost layer (e.g., the topcoat layer) of the coating but for making all other layers of the stent-coating (e.g., the primer layer or the drug-polymer layer) as well. In one embodiment, the stent coating can include only PBT-PEG and be free of any other polymers. The molecular weight of the PEG portion of the PBT-PEG polymer can be between about 300 and about 4,000 Daltons. In PBT-PEG polymer, the units derived from ethylene glycol ("the PEG units") can constitute between about 40 and about 90 molar % of the total PBT-PEG polymer. For example, the PEG units can constitute between about 55 and about 80 molar % of the total PBT-PEG polymer.

The active agent or a drug can include any substance capable of exerting a therapeutic or prophylactic effect in the practice of the present invention. The drug may include small molecule drugs, peptides, proteins, oligonucleotides, and the like. Examples of drugs include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil ((ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon; genetically engineered epithelial cells; rapamycin and structural derivatives or functional analogs thereof, such as 40-O-(2-hydroxy)ethyl-rapamycin (known by the trade name of everolimus available from Novartis), 40-O-(3-hydroxy)propyl-rapamycin, 40-O-[2-(2-hydroxy)ethoxy]ethyl-rapamycin, and 40-O-tetrazole-rapamycin, tacrolimus, and dexamethasone.

The coatings and methods of the present invention have been described with reference to a stent, such as a balloon expandable or self-expandable stent. The use of the coating is not limited to stents, however, and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the present invention can be fuirther illustrated by the following set forth examples.

EXAMPLE 1

A first composition can be prepared by mixing the following components:
(a) between about 1.0 mass % and about 15 mass %, for example, about 2.0 mass % EVAL; and
(b) the balance, DMAC solvent.

The first composition can be applied onto the surface of a bare 13 mm TETRA stent (available from Guidant Corporation) by spraying and dried to form a primer layer. A spray coater can be used having a 0.014 fan nozzle maintained at about 60° C. with a feed pressure of about 0.2 atm (about 3 psi) and an atomization pressure of about 1.3 atm (about 20 psi). About 70 μg of the wet coating can be applied. The primer can be baked at about 140° C. for about 2 hours, yielding a dry primer layer.

A second composition can be prepared by mixing the following components:
(a) between about 1.0 mass % and about 15 mass %, for example, about 2.0 mass % EVAL;
(b) between about 0.05 mass % and about 2.0 mass %, for example, about 1.0 mass % everolimus; and
(c) the balance, DMAC solvent.

The second composition can be applied onto the dried primer layer to form the reservoir layer, using the same spraying technique and equipment used for applying the primer layer. About 400 μg of the wet coating can be applied, followed by drying, e.g., by baking as described above.

A third composition can be prepared by mixing the following components:
(a) between about 1.0 mass % and about 15 mass %, for example, about 2.0 mass % EVAL;
(b) between about 0.5 mass % and about 5.0 mass %, for example, about 1.0 mass % poly(ethylene glycol) having molecular weight of about 17,500; and
(c) the balance, a solvent mixture comprising DMAC and ethanol (EtOH) in a mass ratio DMAC:EtOH of about 4:1.

The third composition can be applied onto the dried reservoir layer to form a topcoat layer, using the same spraying technique and equipment used for applying the primer layer and the reservoir layer. About 200 μg of the wet coating can be applied, followed by drying, e.g., by baking as described above.

The coated stent can be placed in a humidifying chamber for about 24 hours, at a temperature of about 50° C. and relative humidity of about 100%, followed by removing the stent from the humidifying chamber and drying.

EXAMPLE 2

The stent can be coated as described in Example 1, except when preparing the composition for fabricating the topcoat layer, instead of poly(ethylene glycol) having molecular weight of about 17,500, poly(ethylene glycol)-stearate having molecular weight of about 4,000 can be used.

The coated stent can be treated in the humidifying chamber as described in Example 1.

EXAMPLE 3

The stent can be coated as described in Example 1. The coated stent can be can be placed in a refrigerating unit and exposed to a temperature of about −10° C. for about 1 hour. Following the cooling process, the stent can be dried in the ambient atmosphere for about 24 hours.

EXAMPLE 4

A first composition was prepared by mixing the following components:
(a) about 2.0 mass % PBT-PEG; and
(b) the balance, a solvent blend, the blend comprising 1,1,2-trichloroethane and chloroform in a mass ratio between 1,1,2-trichloroethane and chloroform of about 4:1.

The brand of PBT-PEG that was used had about 45 molar % units derived from PBT and about 55 molar % units derived from PEG. The molecular weight of the PEG units was about 300 Daltons. The first composition was applied onto the surface of a bare 13 mm PENTA stent (available from Guidant Corporation) by spraying and dried to form a primer layer. The primer was baked at about 140° C. for about 1 hour, yielding a dry primer layer having solids content of about 100 µg. "Solids" means the amount of the dry residue deposited on the stent after all volatile organic compounds (e.g., the solvent) have been removed.

A second composition was prepared by mixing the following components:

(a) about 2 mass % PBT-PEG;

(b) about 2 mass % everolimus; and (c) the balance, the blend of 1,1,2-trichloroethane and chloroform described above.

The same brand of PBT-PEG as that utilized for making the primer layer was used. The second composition was applied onto the dried primer layer to form the reservoir layer. The second composition was baked at about 50° C. for about 1 hour, yielding a dry reservoir layer having solids content of about 300 µg.

A third composition was prepared by mixing the following components:

(a) about 2.0 mass % PBT-PEG having about 20 molar % units derived from PBT and about 80 molar % units derived from PEG. The molecular weight of the PEG units was about 4,000 Daltons; and (b) the balance, the blend of 1,1,2-trichloroethane and chloroform described above.

The third composition was applied onto the dried reservoir layer to form a topcoat layer. The third composition was baked at about 50° C. for about 2 hours, yielding a dry topcoat layer having solids content of about 100 µg.

EXAMPLE 5

A stent was coated with a primer layer and a reservoir layer as described in Example 4. A composition was prepared, comprising:

(a) about 1.0 mass % PBT-PEG having about 45 molar % units derived from PBT and about 55 molar % units derived from PEG. The molecular weight of the PEG units was about 300 Daltons;

(b) about 1.0 mass % PBT-PEG having about 20 molar % units derived from PBT and about 80 molar % units derived from PEG. The molecular weight of the PEG units was about 4,000 Daltons; and (c) the balance, the blend of 1,1,2-trichloroethane and chloroform described above.

The composition was applied onto the dried reservoir layer and dried to form a topcoat layer, as described in Example 4. The topcoat layer had solids content of about 100 µg.

EXAMPLE 6

A stent was coated with a primer layer and a reservoir layer as described in Example 4. A composition was prepared, comprising:

(a) about 1.0 mass % PBT-PEG having about 45 molar % units derived from PBT and about 55 molar % units derived from PEG. The molecular weight of the PEG units was about 360 Daltons;

(b) about 1.0 mass % PBT-PEG having about 40 molar % units derived from PBT and about 60 molar % units derived from PEG. The molecular weight of the PEG units was about 1,000 Daltons; and (c) the balance, 1,4-dioxane solvent.

The composition was applied onto the dried reservoir layer and dried to form a topcoat layer, as described in Example 4. The topcoat layer had solids content of about 100 µg.

EXAMPLE 7

A stent was coated with a primer layer described in Example 4. A first composition was prepared by mixing the following components:

(a) about 2 mass % PBT-PEG;

(b) about 2 mass % paclitaxel; and (c) the balance, the blend of 1,1,2-trichloroethane and chloroform described above.

The same brand of PBT-PEG as that utilized for making the primer layer was used. The first composition was applied onto the dried primer layer and dried to form a reservoir layer, as described in Example 4. The reservoir layer had solids content of about 300 µg.

A second composition was prepared by mixing the following components:

(a) about 1.5 mass % PBT-PEG having about 45 molar % units derived from PBT and about 55 molar % units derived from PEG. The molecular weight of the PEG units was about 300 Daltons;

(b) about 0.5 mass % PBT-PEG having about 20 molar % units derived from PBT and about 80 molar % units derived from PEG. The molecular weight of the PEG units was about 4,000 Daltons; and (c) the balance, the blend of 1,1,2-trichloroethane and chloroform described above.

The composition was applied onto the dried reservoir layer and dried to form a topcoat layer, as described in Example 4. The topcoat layer had solids content of about 100 µg.

EXAMPLE 8

A stent was coated with a primer layer and a reservoir layer as described in Example 7. A composition was prepared, comprising:

(a) about mass 1.0% of PBT-PEG having about 45 molar % units derived from PBT and about 55 molar % units derived from PEG. The molecular weight of the PEG units was about 300 Daltons; and (b) 1.0 about mass % PBT-PEG having about 20 molar % units derived from PBT and about 80 molar % units derived from PEG. The molecular weight of the PEG units was about 4,000 Daltons;

(c) the balance, the blend of 1,1,2-trichloroethane and chloroform described above.

The composition was applied onto the dried reservoir layer and dried to form a topcoat layer, as described in Example 7. The topcoat layer had solids content of about 100 µg.

EXAMPLE 9

A 12 mm VISION stent (available from Guidant Corp.) was coated with a primer layer described in Example 4. A first composition was prepared by mixing the following components:

(a) about 2 mass % everolimus; and (b) the balance, the blend of acetone and xylene in a mass ratio between acetone and xylene of about 2:3.

The first composition was applied onto the dried primer layer to form the reservoir layer. The first composition was baked at about 50° C. for about 1 hour, yielding a dry reservoir layer having solids content of about 200 μg.

A second composition was prepared, comprising:

(a) about 2.0 mass % of PBT-PEG having about 45 molar % units derived from PBT and about 55 molar % units derived from PEG. The molecular weight of the PEG units was about 300 Daltons; and (b) the balance, the blend of 1,1,2-tricloroethane and chloroform described above.

The second composition was applied onto the dried reservoir layer and dried to form a topcoat layer, as described in Example 4.

The coating compositions discussed in Examples 1–9 are summarized in Table 1.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

TABLE 1

Stent Coatings of Examples 1–9

| Example | Primer Polymer | Reservoir Polymer | Drug | Topcoat Polymer |
|---|---|---|---|---|
| 1 | EVAL | EVAL | everolimus | 1. EVAL<br>2. PEG (EVAL:PEG ratio is 2:1) |
| 2 | EVAL | EVAL | everolimus | 1. EVAL<br>2. PEG-stearate (EVAL:PEG-stearate ratio is 2:1) |
| 3 | EVAL | EVAL | everolimus | 1. EVAL<br>2. PEG (EVAL:PEG ratio is 2:1) |
| 4 | PBT-PEG<br>PBT - 45 mol. %<br>PEG - 55 mol. %<br>PEG's MW*⁾ = 300 | PBT-PEG<br>PBT - 45 mol. %<br>PEG - 55 mol. %<br>PEG's MW = 300 | everolimus | PBT-PEG<br>PBT - 20 mol. %; PEG - 80 mol. %<br>PEG's MW = 4,000 |
| 5 | PBT-PEG<br>PBT - 45 mol. %<br>PEG - 55 mol. %<br>PEG's MW = 300 | PBT-PEG<br>PBT - 45 mol. %<br>PEG - 55 mol. %<br>PEG's MW = 300 | everolimus | (1) PBT-PEG<br>PBT - 45 mol. %; PEG - 55 mol. %<br>PEG's MW = 300<br>(2) PBT-PEG<br>PBT - 20 mol. %; PEG - 80 mol. %<br>PEG's MW = 4,000<br>Ratio (1) PBT-PEG:(2) PBT-PEG = 1:1 |
| 6 | PBT-PEG<br>PBT - 45 mol. %<br>PEG - 55 mol. %<br>PEG's MW = 300 | PBT-PEG<br>PBT - 45 mol. %<br>PEG - 55 mol. %<br>PEG's MW = 300 | everolimus | (1) PBT-PEG<br>PBT - 45 mol. %; PEG - 55 mol. %<br>PEG's MW = 300<br>(2) PBT-PEG<br>PBT - 40 mol. %; PEG - 60 mol. %<br>PEG's MW = 1,000<br>Ratio (1) PBT-PEG:(2) PBT-PEG = 1:1 |
| 7 | PBT-PEG<br>PBT - 45 mol. %<br>PEG - 55 mol. %<br>PEG's MW = 300 | PBT-PEG<br>PBT - 45 mol. %<br>PEG - 55 mol. %<br>PEG's MW = 300 | Paclitaxel | (1) PBT-PEG<br>PBT - 45 mol. %; PEG - 55 mol. %<br>PEG's MW = 300<br>(2) PBT-PEG<br>PBT - 20 mol. %; PEG - 80 mol. %<br>PEG's MW = 4,000<br>Ratio (1) PBT-PEG:(2) PBT-PEG = 3:1 |
| 8 | PBT-PEG<br>PBT - 45 mol. %<br>PEG - 55 mol. %<br>PEG's MW = 300 | PBT-PEG<br>PBT - 45 mol. %<br>PEG - 55 mol. %<br>PEG's MW = 300 | Paclitaxel | (1) PBT-PEG<br>PBT - 45 mol. %; PEG - 55 mol. %<br>PEG's MW = 300<br>(2) PBT-PEG<br>PBT - 20 mol. %; PEG - 80 mol. %<br>PEG's MW = 4,000<br>Ratio (1) PBT-PEG:(2) PBT-PEG = 1:1 |
| 9 | PBT-PEG<br>PBT - 45 mol. %<br>PEG - 55 mol. %<br>PEG's MW*⁾ = 300 | N/A | everolimus | PBT-PEG<br>PBT - 45 mol. %<br>PEG - 55 mol. %<br>PEG's MW*⁾ = 300 |

*⁾MW is an abbreviation for "molecular weight"

What is claimed is:

1. An implantable medical device, comprising a coating, the coating including a poly(butylene terephthalate-co-ethylene glycol)polymer,
   wherein the poly(butylene terephthalate-co-ethylene glycol)polymer comprises hydrophilic units derived from ethylene glycol between about 40% and about 90 molar % of the total units of the PBT-PEG polymer, and
   wherein the coating is formed-by a method comprising a post-coating process to cause the hydrophilic units to be extracted or bloom to the coating-air interface.

2. The implantable medical device of claim 1, wherein the implantable medical device is a stent.

3. The imp lantable medical device of claim 1, wherein the ratio between the units derived from ethylene glycol and the units derived from butylene terephthalate is between about 0.67:1 and 9:1.

4. The implantable medical device of claim 1, additionally including a therapeutic substance.

5. The implantable medical device of claim 4, wherein the therapeutic substance is selected from a group of paclitaxel, docetaxel, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, and 40-O-tetrazole-rapamycin, and analogs thereof.

6. The implantable medical device of claim 1, wherein the ethylene glycol units constitute 40 to 90 mole % of the polymer.

7. The implantable medical device of claim 1, wherein the ethylene glycol units constitute 55 to 80 mole % of the polymer.

8. An implantable medical device, comprising a coating, the coating including a first region comprising poly(butylene terephthalate-co-ethylene glycol) and a second region comprising poly(butylene terephthalate-co-ethylene glycol), wherein the mole % of the ethylene glycol is higher in the second region than the first region, wherein units of ethylene glycol in poly(butylene terephthalate-co-ethylene glycol) of the first region or units of ethylene glycol in poly(butylene terephthalate-co-ethylene glycol) of the second region were extracted or bloomed to the coating-air interface.

9. The implantable medical device of claim 8, wherein the device is a stent.

10. The implantable medical device of claim 8, wherein the second region is over the first region.

11. The implantable medical device of claim 8, wherein the second region is the outermost layer of the coating.

12. The implantable medical device of claim 8, wherein the second region is the outermost layer of the coating and the first region is a reservoir layer including a drug and which is positioned beneath the outermost layer.

13. The implantable medical device of claim 8, wherein the coating additionally includes a therapeutic substance.

14. The implantable medical device of claim 13, wherein the therapeutic substance is selected from a group of paclitaxel, docetaxel, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, and 40-O-tetrazole-rapamycin, and analogs thereof.

* * * * *